United States Patent [19]

Kussick

[11] Patent Number: 4,773,853

[45] Date of Patent: Sep. 27, 1988

[54] ORAL ORTHOPEDIC APPLIANCE

[76] Inventor: Leon Kussick, 1 Surrey La., Livingston, N.J. 07039

[21] Appl. No.: 118,882

[22] Filed: Nov. 9, 1987

[51] Int. Cl.$^4$ ................................................ A61C 7/00
[52] U.S. Cl. ........................................................ 433/6
[58] Field of Search ........................................ 433/6, 7

[56] References Cited

U.S. PATENT DOCUMENTS 3,478,729 11/1969 Shuliday ................................. 433/6
3,478,742 11/1969 Bohlmann ............................. 433/6

Primary Examiner—Robert Peshock

[57] ABSTRACT

A single piece appliance for correcting oral abnormalities without wires or bands has a segment engaging anterior dentition of the maxillary arch and a pair of spaced segments extending downwardly and posteriorly from the anterior dentition engaging segment at a predetermined angle with respect to the anterior dentition engaging segment. Each downwardly extending segment includes a labial facing surface that forms an inclined plane at the predetermined angle with the anterior dentition engaging segment adapted to contact the lingual aspect of the incisal edges of selected teeth on the mandibular arch so that the lower jaw is urged forward and steeply upward while the upper jaw is urged backward when necessary. At least one longitudinal ridge extends across each labial facing surface at a prescribed location along the labial facing surface to restrict the forward and upward movement of the mandible when the incisal edges of selected teeth of the mandibular arch are in contact with the labial facing surface.

19 Claims, 3 Drawing Sheets

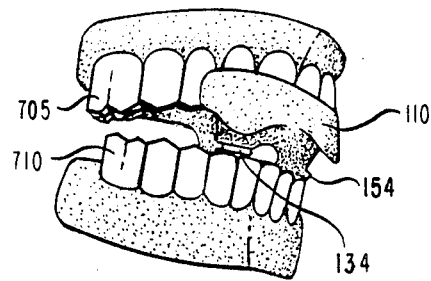
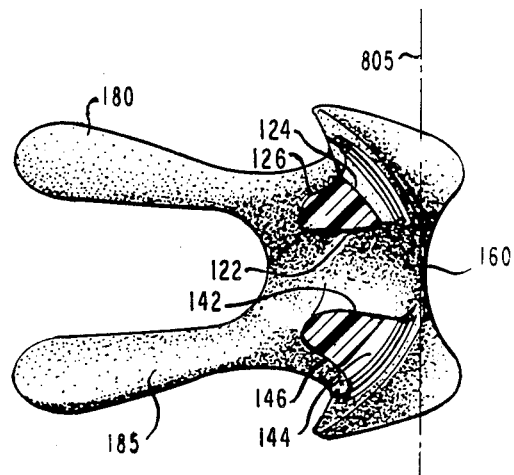
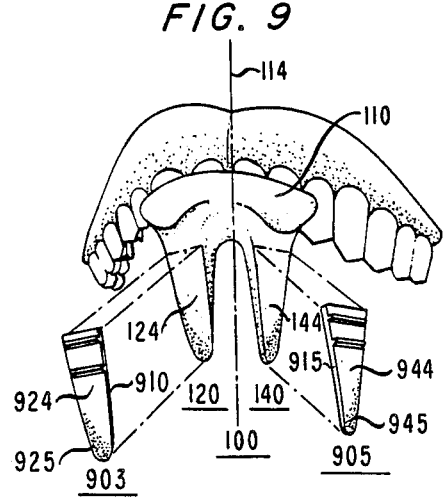

ORAL ORTHOPEDIC APPLIANCE

TECHNICAL FIELD

My invention relates to devices for correcting oral abnormalities and, more particularly, to an appliance adapted to correct Class I, Class II Division 1 and Class II Division 2 deep bite type malocclusions.

BACKGROUND OF THE INVENTION

As is well known, a Class II Division 1 type malocclusion is characterized by a mandibular retrusion and/or a maxillary protrusion where the lower molars are posterior to the upper molars and by a deep bite and severe overjet. In a Class II Division 2 malocclusion, there is a less severe mandibular retrusion and/or a maxillary protrusion, a very deep bite, a mild to moderate overjet and a lingual tipping of the upper incisors. The molars are in substantially normal relationship in a Class I malocclusion, but there is a deep bite as well as a mild overjet. Such malocclusions are often accompanied by positional irregularities and crowding of the anterior teeth. These conditions usually result in an abnormal bite, interference with efficient mastication and an unfavorable appearance. Malocclusions are generally treated between the ages of seven to fourteen while the alveolus and the bones of the jaws are highly susceptible to change.

Many orthopedic applicances have been proposed to correct these types of malocclusions. The Frankel appliance described in "Removable Orthodontic Appliances" by T. M. Graber and Bedrich Neumann published by W. B. Saunders Company, 1977 is relatively complex having two buccal shields, lip pads with connecting wires, a labial wire and two canine wire loops on the labial side, a heavy palatal wire with occlusal extension supports on the maxillary molars from the lingual side and a lingual wire bow with U loops on the lower front teeth of the mandible. The well known Bimler appliance is similar in some respects to the Frankel appliance and also has a complex arrangement of acrylic and wires to accomplish mandibular repositioning. It is generally recommended that these appliances be worn 23-24 hours a day which may cause inconvenience or discomfort to the wearer. The complex arrangement of wires is also prone to distortion through bending and breakage and may be in irritating contact with soft tissue. Both appliances are loose fitting in the mouth when closed and fall downward freely when the mouth is opened and exhibit extensive contact of acrylic against soft tissue.

The Bionator type appliance also described in the aforementioned book is a bulky acrylic structure with palatal wires and acrylic that rest on gum behind the lower anterior teeth. The device is free falling as are all functional type appliances, touches soft tissue extensively, is confining to the tongue so that it may be difficult to speak and should be worn twenty three hours a day. The aforementioned appliances are adapted to induce a patient to rest on the appliance in a forward and downward protrusive position with the lower jaw to correct a retrusive mandible. The effect is to extend the position of the lower jaw forward and downward rather than to bring the maxillary and mandibular arches into more correct and esthetic positions with respect to each other.

U.S. Pat. No. 4,382,783 issued to Farel A. Rosenberg June 18, 1982 discloses an intraoral dental appliance to correct retrusive mandibles in which two hinges with telescoping members are used to join an upper molar and a lower molar on both sides of the mouth. The point of attachment of each lower hinge is somewhat forward on the lower molar than the corresponding upper molar when the appliance is installed. As a consequence, closure of the mouth forces the lower jaw forward and a permanent change in the muscle-resting length and induces changes in the lower jaw and its joint. The appliance, however, restricts jaw movement, requires permanent attachment to both upper and lower teeth, and uses cemented bands which may disengage from the teeth thereby distorting the hinges and irritating soft tissue.

U.S. Pat. No. 4,439,149 issued to John Devincenzo Mar. 27, 1984 discloses a removable orthodontic appliance that includes upper and lower plates which contact each other along vertically oriented indexing planes. The tendency of the lower jaw to retract is opposed by the indexing planes of the upper plate which are located in the molar areas. The indexing planes of the upper plate bear against the indexing planes of the lower plate to maintain the jaw in a jutting forward position while not interfering with the opening and closing of the jaw. The Devincenzo appliance is operative, however, to deflect the mandible down and forward rather than to effect a more normal final relation between the maxillary and mandibular arches. It is used primarily to correct some Class II Division 1 malocclusions with deep bites where there is no crowding of the teeth as is the case with most functional appliances.

U.S. Pat. No. 4,671,766 issued to John J. Norton June 9, 1987 discloses an intraoral orthotic for treatment of temporomandibular joint problems which consists of two halves, one in the maxillary arch and one in the mandibular arch. Both halves have wings projecting from them which interlock upon closing of the mouth. When each half is positioned in its arch attached to the teeth and the mouth is closed, the wings on the two pieces engage in a predetermined position to allow the meniscus to be in a proper therapeutic position and to stabilize the surrounding muscles of mastication. The arrangement requires both an upper and lower half which may interfere with normal mouth functions and is adapted to manipulate the mandible downward and forward so that it can result in an extended mandible rather than a repositioning of both the maxillary and mandibular arches to a more normal relationship.

U.S. Pat. No. 4,433,956 issued to John W. Witzig Feb. 28, 1984 discloses an orthopedic corrector for correction of Class II Division 1 malocclusions which comprises an acrylic anterior segment molded to fit the lower mouth and anterior dentition and two acrylic posterior segments molded to fit the upper mouth and dentition of a patient. An expansion screw connects each posterior segment to the anterior segment for expandable movement between the anterior segment and the posterior segments. The appliance is expanded by adjusting the expansion screw in stages to maximize the utilization of corrective lower jaw movements which results from the anchoring of the orthopedic appliance in the patient's upper mouth. The Witzig appliance requires an upper section connected to the maxillary arch and a lower section connected to the mandibular arch which are likely to interfere with normal mouth functions. Wires are also needed for attachment of the components of the appliance to the teeth which wires may irritate soft tissue or bend to distort the appliance. Further, 23 to 24 hour wear may be necessary and adjustment of the device by the patient or other lay persons is relied on for effective therapy. The appliance also tends to irritate gums and tip the lower front teeth forward. None of the aforementioned appliances is adapted to correct moderate to severe crowding of the lower anterior teeth and all are designed to be loose fitting.

The article "Bone Remodeling, A New Orthodontic Approach for Interceptive and Total Mixed Dentition Therapy" by Leon Kussick appearing in the ASDC Journal of Dentistry for Children, January-February, 1978 discloses an orthopedic appliance comprising a single acrylic broad palatal plate removably attached to the upper teeth which may require support by a wire assembly. The broad one piece descending acrylic plate extends from the maxillary arch to define an inclined plane angled to contact the lingual edges of lower anterior teeth so that the mandible can be moved forward and upward while the maxillary alveolar arch is retracted. The corrective action is controllable and affects both the maxillary and mandibular arches but the appliance is bulky, may require wires in contact with soft tissue of the maxillary arch and successful use requires individual design, laboratory construction and considerable adjustment of the appliance for each patient by a highly skilled and specially trained dentist or orthodontist. It is an object of the invention to provide an improved oral appliance to relocate the maxillary and mandibular arches that is adapted to correct malocclusions for a large category of patients with more accurate jaw positioning control and without requiring highly specialized orthodontic skills for successful use.

BRIEF SUMMARY OF THE INVENTION

The invention is directed to an oral corrective appliance which has an upper lateral segment engaging the anterior dentition of the upper jaw and a pair of spaced segments descending towards the lower jaw. The descending segments are pyramidal in shape with base portions fixed to the upper segment. Each of the descending segments has a substantially flat labial facing surface angled with respect to the upper segment and is of a length that maintains the descending segments posterior to the anterior teeth of the lower jaw but avoids contact with lingual tissue of the lower jaw. Each substantially flat surface is adapted to steeply contact the lingual aspect of the incisal edges or the cuspid tips in the lower jaw at a prescribed angle with respect to the tooth. The substantially flat surface of each descending segment has at least one longitudinal ridge spaced from the top of the lateral segment to control the relative placement of the lower jaw with respect to the upper jaw when the appliance engages the upper jaw front teeth.

According to one aspect of the invention, the substantially flat surface of each descending segment has a plurality of longitudinal ridges each spaced from the lateral segment to treat one of the class I, class II Division 1 and class II Division II malocclusions.

According to another aspect of the invention, the angle of contact between the lower edge of the descending segment with the lingual aspect of the lateral incisal edge or the cuspid tip in the mandibular arch is selected to correct misalignment of the contacted tooth or teeth.

According to yet another aspect of the invention, the appliance further comprises at least one segment fixed to the anterior dentition fitting segment that extends lingually in the palatal area and is contoured to prevent swallowing of the appliance while avoiding contact with palatal soft tissue.

According to yet another aspect of the invention, each descending segment is in the shape of a triangular pyramid. The surfaces are shaped to prevent contact with soft tissue of the mandibular arch.

In an embodiment of the invention, a basic appliance made of acrylic adapted to fit a wide range of mouths is molded with a plurality of longitudinal ridges on the descending segments. Each ridge is located in accordance with the type of malocclusion. The upper segment is adapted to be firmly anchored in engagement with the labial side of the front teeth of the upper jaw. The descending segments are operative to contact the rear incisal surfaces of selected anterior lower jaw teeth at an angle which urges the patient to move the lower jaw forward and upward while urging the upper jaw backward when required. The longitudinal ridge selected for the type of malocclusion to be corrected controls the extent of travel of the lower jaw and teeth up the incline of the flat surface of the descending segments. The other longitudinal ridges not applicable to the malocclusion are removed. Swallowing of the device is prevented by the long palatal area segments extending posteriorly into the mouth from the lateral segment and positioned to avoid contact with the palatal arch tissue. Advantageously, contact between the device and any soft tissue is avoided and the space between the descending segments allows free movement of the tongue for easier swallowing and better speech. The upper and lower jaws are both urged into alignment with a prefabricated standard appliance readily modifiable by a person of moderate skill rather than being custom designed, laboratory constructed, and fitted and adjusted by a highly skilled practitioner. Advantageously, more accurate jaw positioning control is achieved, no wires, buccal shields or expansion mechanisms are used and there is no irritation of soft tissue or distortion of the appliance.

DESCRIPTION OF THE DRAWING

FIG. 7 is a perspective view of the appliance of FIG. 1 installed in a mouth illustrating its relationship to the upper and lower jaws;

FIG. 8 is a cross-section along lines 8—8 in FIG. 2; and

FIG. 9 shows an exploded view of the appliance of FIG. 1 to which thickness increasing wedges are added to the front of the appliance.

DETAILED DESCRIPTION

Figure 1:
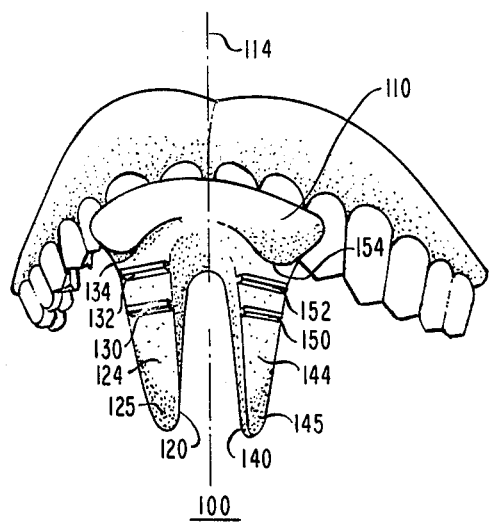
FIG. 1 depicts a perspective view of an oral corrective appliance illustrative of the invention installed on a maxillary arch.

FIG. 1 shows a perspective view of an orthodontic appliance illustrative of the invention in tight engagement with anterior teeth of a maxillary arch. The appliance generally denoted as 100 is made of acrylic or other similar non-toxic material and includes an upper segment 110 disposed laterally in the front of the mouth. Segment 110 extends laterally across the maxillary arch and is adapted to engage the labial and lingual surfaces of teeth along the anterior of the maxillary arch. Segments 120 and 140 extend downward from segment 110 and are angled toward the posterior of the mouth to end lingual to the anterior dentition of the mandibular arch. These segments are generally pyramidal in shape, and are spaced apart by arc shaped section 160. As shown, segments 120 and 140 are substantially parallel and disposed symmetrically about center line 114 of lateral running segment 110. Typically, the descending segments are 24 to 26 mm long and their apexes of the descending segments are spaced 4 to 8 mm apart. Labial facing surface 124 of segment 120 and labial facing surface 144 of segment 140 are substantially flat except for beveled portions 125 and 145 on surfaces 124 and 144. The beveled portion avoids contact between the labial facing surface and lingual soft tissue of the mandibular arch. Each labial facing surface forms a ramp having a prescribed angular relationship to lateral segment 110. Labial facing surface 124 has longitudinal ridges 130, 132 and 134 at predetermined locations therealong. Similarly, labial facing surface 144 includes corresponding longitudinal ridges 150, 152 and 154. These longitudinal ridges are positioned along the labial facing surfaces in accordance with the type of malocclusion to be treated.

Figure 2:
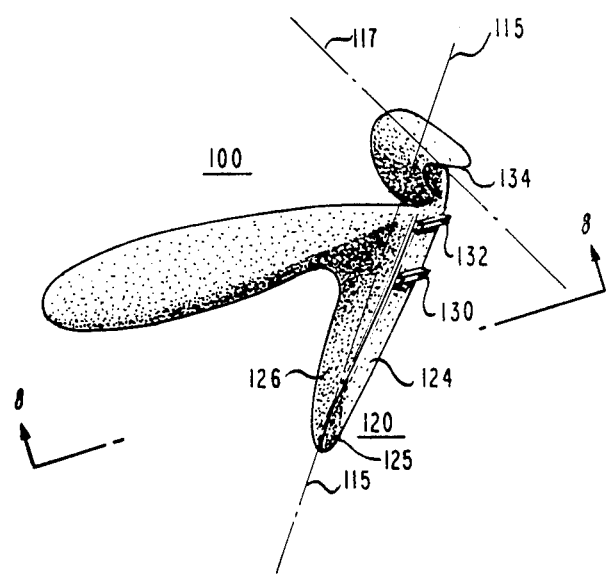
FIG. 2 is an elevational view of the appliance on FIG. 1 from the right side.
Figure 3:
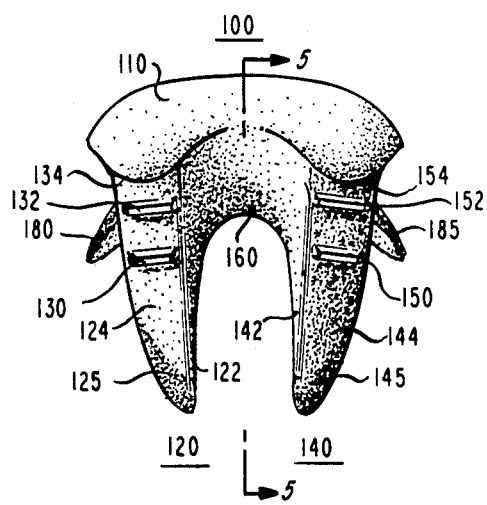
FIG. 3 is a front elevational view of the appliance of FIG. 1.
Figure 4:
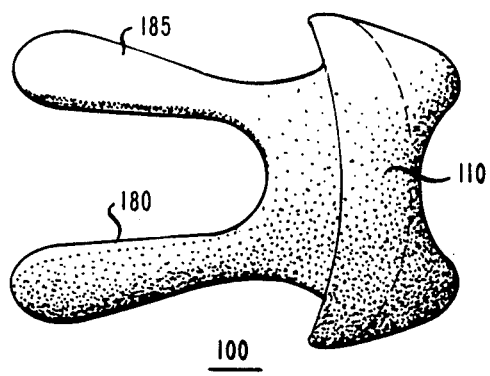
FIG. 4 is a top elevational view of the appliance on FIG. 1.

Appliance 100 prior to installation in a particular case is shown in side, front and top views in FIGS. 2, 3 and 4. As illustrated in the side view of FIG. 2, descending segment 120 follows line 115 and is angled with respect to the maxillary fitting segment 110 which follows line 117 so that its front surface 124 is a steep inclined plane. The inclined plane is adapted to contact the lingual edges of the incisors in the mandibular arch as the mouth is brought from an open position to a closed position against a longitudinal ridge with the appliance being worn. Such contact is effective to urge a retrusive lower jaw forward and upward while urging the upper jaw backwards when appropriate.

The appliance is operative to cause tension on and adjustment of the muscle attachments on the periosteum (the thin connective tissue layer surrounding the bones) of growing children which is followed by vertical and anterior relocation of the mandible. When the attachments and rest positions of the mandibular musculature are temporarily altered by the increased tension induced by wearing of the appliance, there is a distal (backward) condylar adaptation into the temporary space created in the fossa (joint of the jaw) and also an adaptive increase of the localized vertical alveolar bone deposition. This new bone and the buccal teeth within it fill the potential and temporarily created buccal open bits in the posterior region, reestablishing the new occlusion and also increasing the maxillary arch width. As a result, the mandibular and maxillary arches and dentition are placed into a more normal, stable relationship while correcting deep bite.

There are three longitudinal ridges on each descending segment 120 and 140 in the appliance of FIGS. 2, 3 and 4. Each is located along surface 124 and surface 144 to provide a stop for the forward and upward motion of the lower jaw according to the malocclusion to be treated. When initially inserted, the two ridges on each descending segment that are not related to the wearer's type of malocclusion are removed by grinding them away or other method. The remaining ridges are made broader to provide more positive stopping action by adding acrylic thereto. As shown in the front view of FIG. 3, segments 120 and 140 are substantially parallel spaced apart by arc 160 so that they are symmetrical about center line 114. Descending segment 120 is a triangular pyramid having labial facing surface 124, medial surface 122 shown in FIG. 3 and lingual facing surface 126 shown in FIG. 2. Similarly, segment 140 has labial facing surface 144, medial surface 142 shown in FIG. 3 and lingual facing surface 146 not shown.

The side surfaces 122 and 126 and 142 and 146 are contoured by beveling or angling to avoid contact with lingual anterior mandibular soft tissue. In accordance with the invention, the angular relationship between labial facing side 124 and the contacted mandibular anterior tooth may be arranged so that side 124 corrects positional irregularities of the tooth. Similarly, the angle between labial facing side 144 of descending segment 140 and the contacted mandibular anterior tooth may be arranged to correct positional irregularities of the contacted mandibular anterior tooth. Such angling of the labial facing surface 124 is independent of the angling of labial facing surface 144. If the positional irregularity of a single tooth is to be corrected the labial surface may be grooved in the line of ascent up the ramp to better assure proper repositioning of the tooth.

FIG. 8 is a cross-section of the appliance viewed along lines 8—8 in FIG. 1. Referring to FIG. 8, each of descending segments 120 and 140 has a pyramid cross-section with a base integral to lateral segment 110 and a rounded apex which will fall lingual to the anterior teeth of the lower jaw. Labial facing surface 124 of segment 120 joins medial facing surface 122 and lingual facing surface 126. Surfaces 122 and 126 join posteriorly to labial facing surface 124. Similarly, Labial facing surface 144 of segment 140 joins lingual facing surface 146 and medial facing surface 142. Surfaces 142 and 146 join posteriorly to labial facing surface 144. An open space is maintained between the descending segments by arch 160 so that tongue motion is possible for speech, swallowing or other oral activity.

The angle that each labial facing surface 124 and 144 makes with front line 805 shown in FIG. 8 is adjustable independent of the angle of the inclined plane with the palatal arch so that force on the contacted mandibular anterior tooth is directed to correct the tooth's position and orientation. Horizontal segments 180 and 185 extend posteriorly from top segment 110 when the appliance is in the mouth. These horizontal segments prevent swallowing of the appliance by the wearer. They are located below the palate and are shaped to be close to but not touching the palate to avoid contact with soft tissue and prevent any irritation thereof. The spacing between segments 180 and 185 permits the wearer be more comfortable while speaking, swallowing and other during other oral activity.

Figure 5:
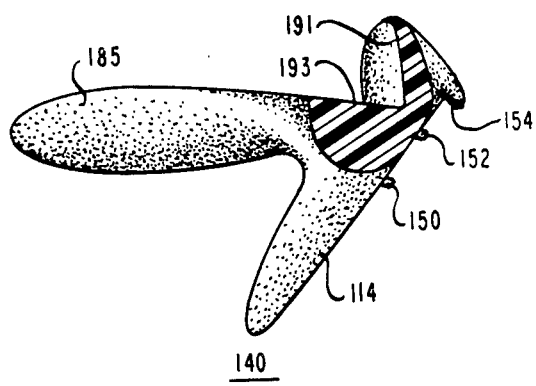
FIG. 5 is a cross section of the upper segment of the appliance of FIG. 3 taken along lines 5—5 to illustrate how the appliance is anchored to the anterior teeth of the upper jaw.

The appliance may be made by pouring uncured acrylic into a silicone rubber mold or by other methods well known in the art. As it is removed from the mold, the appliance conforms to a standard size or one of several standard sizes and is of the shape shown in FIGS. 2, 3, and 4. Upper segment 110 has a cross section shown in FIG. 5 taken along lines 5—5 in FIG. 3. Arcuate edge 191 is adapted to engage the labial surfaces of anterior dentition of the upper arch and, at the same time, surface 193 on the bottom to the back of lateral segment 110 is adapted to hold an acrylic insert section which insert section engages the lingual surfaces of these teeth. To obtain tight engagement with the anterior dentition of the maxillary arch, soft uncured acrylic is put on surfaces 191 and 193 of the standard size appliance shown in FIG. 5 to fill in the space therebetween. An impression of the labial and lingual surfaces of the anterior dentition of the maxillary arch is then made by methods well known in the art. With an acrylic impression of the wearer's anterior teeth thus formed, the appliance is then removed in one or two minutes and the newly added acrylic is allowed to bench cure. After curing, it accurately engages the undercut high up on the labial surfaces of the anterior teeth and extends tightly around a portion, e.g. ⅜, of the lingual surfaces of these teeth. In this manner, surfaces are shaped with respect to the anterior dentition so that the appliance is tightly anchored to the maxillary anterior dentition but removable therefrom with some effort. Contact with the lingual gum tissue, however, is avoided. Consequently, the need for a wax bite and models of the upper and lower teeth along with outside laboratory construction is obviated. Although firmly anchored in the mouth when worn, the appliance may be removed daily by the wearer as required. Advantageously, no wires or bands are required so there is no problem of wire breakage and or distortion of the appliance leading to possible injury of soft tissue. Of greater importance, the appliance can be worn comfortably on a regular basis to avoid non-response or relapse.

As the appliance is worn, the mandibular incisors slide up the steep inclined plane to effect a correction of both the jaw position and/or lower teeth crowding. Because of the steep incline attainable with the appliance as shown herein, the arch width expands and the maxillary alveolus retracts if needed in Class II Division 1 cases. The needed corrective action is controlled by the muscle tension created by positioning of the lower jaw against the selected ridge of the inclined descending segment. In the case of a Class II Division 2 malocclusion, the position of the longitudinal ridge must be located below the position of a longitudinal ridge for Class I and class II Division 1 malocclusions so that longitudinal ridges 130 and 150 are used. In the case of a Class II Division 1 malocclusion, the longitudinal ridge location is above and forward of those for the Class II Division 2 and Class I malocclusions. Consequently, longitudinal ridge 134 and 154 are selected. A class I malocclusion requires that the longitudinal ridge be located at a point along the inclined plane surface 124 or 144 intermediate the locations for Class II Division 1 and Division 2 malocclusions so that ridges 132 and 152 are used. Once the appropriate longitudinal ridge is selected, the other ridges are removed by grinding. The selected ridge is reinforced and made operative to stop movement of the lower incisors beyond a controlled point up the inclined plane of surface 124 of segment 120 and surface 144 of segment 140. Alternatively, the appliance may be made with only one longitudinal ridge for a predetermined type of malocclusion. Ridge 130 in FIG. 2 is typically located 15 to 16 mm above the apex of the descending segment 120. Ridge 132 is spaced about 4 mm from ridge 130 and ridge 134 is spaced 5 mm from ridge 132.

It is apparent that the selection of the angle of the inclined plane and location of longitudinal ridges to provide corrective action require a high degree of skill and experience in making the appliance for a particular individual and in adjusting its parameters. Such skill and experience may not be possessed by the ordinary practitioner. According to the invention, a standard appliance is constructed that is generally adapted to fit a wide range of individuals and to a correct various types of malocclusions. The critical parameters relating to the angle of the inclined plane, the angle of the inclined plane bevel and the location of the longitudinal ridges are preset before the appliance is installed. Relatively minor adjustments are made in each particular case by shaping the acrylic to adjust the angle of the incline, the bevels 125 and 145 or the location of the longitudinal ridges to permit effective treatment of the individual malocclusion and/or positional irregularities of the tooth or jaw.

The longitudinal ridges are precisely located on the initial appliance and it is only necessary to select the ridge required for the particular case. Adjustment of the position of the ridge for a given patient may be readily made as treatment progresses by grinding the longitudinal ridge and/or adding acrylic to the inclined planes at the desired locations needed for continued correction. Thickness increasing elements such as wedges 903 and 905 shown in FIG. 9 may be fitted over descending sections 120 and 140 to provide additional adjustment so that the shape of these descending segments may be modified and the thickness may be increased. Similarly, the angles that surfaces 124 and 144 make with respect to the palatal plane are accurately preset for a standard situation. Since the appliance is made of acrylic or other suitable plastic material, minor modifications in the angle of the inclined plane and ridge location are readily made for a particular case. Changes may be effected by grinding or by adding acrylic to the descending segments of the appliance or adding the wedges of FIG. 9 and then grinding to modify the angle. Thus, the practitioner is relieved of the task of forming an initial appliance by means of a wax bite and models of the teeth and laboratory construction and the highly skilled task of accurately setting the parameters of the appliance to fit the patient's individual needs.

Figure 6:
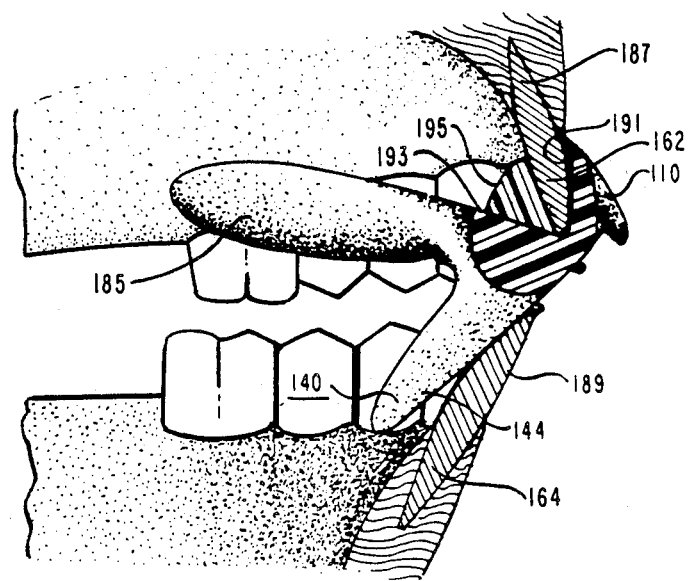
FIG. 6 is a diagrammatic cross-section of the appliance of FIG. 1 in a mouth to illustrate its operation.

FIG. 6 is a diagrammatic view of the appliance anchored to the upper jaw teeth comprising crown sections 162 and root sections 187 in the maxillary arch. Lateral segment 110 frictionally engages crowns 162 on the maxillary arch. As indicated in FIG. 6, surface 191 of the lateral segment 110 engages the labial surface of crowns 162 while an edge of acrylic element 195 engages a portion of the lingual surface of the crowns. Horizontal segment 185 extends posteriorly from segment 110 offset from palatal tissue. Descending segment 140 is steeply angled and is of a length that assures it will always have a portion posterior to the mandibular lateral incisor crown 189 of the tooth comprising crown section 189 and root section 164.

As the jaws are moved to a more closed position, the incisal edge of crown 189 contacts the labial facing surface of the descending segment. This contact is maintained with the inclined plane so that the mandible is urged forward and upward. At the same time, the upper jaw is urged posteriorly when required. The effect is to cause the bone and muscle structure to be modified so as to result in a permanent respositioning of the maxillary and mandibular arches for a correct finished profile position. Accurate control of the muscle and bone modification is maintained by the properly selected longitudinal ridge. As treatment progresses both the longitudinal ridge location and the angle of the inclined plane can be easily adjusted.

In the event that the mandible must be placed further forward and/or upward with respect to the maxillary arch than permitted by the descending segments, wedge shaped plates may be joined to the front of the descending segments 124 and 144 to effect the needed repositioning. FIG. 9 shows the appliance of FIG. 1 and a pair of wedge shaped plates 903 and 905 which are to be adhered to the labial surfaces 124 and 144, respectively. Wedges 903 and 905 have the same general shape of the labial surfaces and are adhered thereto by placing uncured acrylic therebetween. The wedges are effective to extend the thickness of the labial aspect of the descending segments to provide more greater range of corrective repositioning. Wedge 903 has a back surface 910 and a flat labial facing surface 924 of substantially the same shape as the labial facing surface of descending segment 120 to which it is joined. It also includes a bevel portion 925 that prevents contact with soft tissue. Similarly, wedge 905 has a back surface 915, a flat labial facing surface 944 of substantially the same shape as the labial facing surface of descending segment 140 to which it is joined and includes a bevel portion 945 that prevents contact with soft tissue. The back surface of each wedge is shaped to adhere to the labial surface of the descending segment. In effecting an increased thickness of the descending segment, wedge 903 is placed directly over labial facing surface 124. Similarly, wedge 905 is placed directly over labial facing surface 144. The wedge 903 may be moved to one side or the other so that the lingual incisal edge of an adjacent tooth to the one affected by labial surface 124 also contacts the appliance thereby permitting realignment of the adjacent tooth. The same arrangement may be accomplished with wedge 905 on labial surface 144.

FIG. 7 is a perspective view of the appliance in a mouth that is in a more closed position with the lower incisors contacting longitudinal ridges 134 and 154. As shown, the relative positions of matching upper and lower molars 705 and 710 are altered by the inclined plane of the descending segments so that lower molar 710 is moved forward of the upper molar 705. From FIGS. 6 and 7, it is readily seen that very accurate control of the jaw position is maintained by the appliance. I have found that it is only necessary for a patient to wear the appliance for 2 to 3 hours a day and at night to obtain effective treatment. Yet no wires, bands, screws or accessory acrylic parts are used. There is no contact with soft tissue and there is no need to place a very bulky or very delicate object in the mouth.

The invention has been shown and described with reference to a particular embodiment thereof. It is to be understood that modifications and changes may be made by those skilled in the art without departing from the spirit and scope of the invention.

What is claimed is:

1. An appliance for correcting oral malocclusions comprising:
   a segment for engaging anterior dentition or the maxillary arch;
   a pair of spaced segments extending downwardly and posteriorly from the anterior dentition engaging segment at a predetermined angle with respect to the anterior dentition engaging segment;
   each downwardly extending segment including a labial facing surface forming an inclined plane at said predetermined angle with said anterior dentition engaging segment for contacting the lingual aspect of selected teeth on the mandibular arch; and
   at least one longitudinal ridge extending across each labial facing surface at a prescribed location along said labial facing surface to restrict the forward and upward movement of the mandible when said selected teeth of the mandibular arch are in contact with the labial facing surface.

2. An appliance for correcting oral malocclusions according to claim 1 wherein each downward and posteriorly extending segment comprises a generally pyramidal shaped segment having a base portion at the lower end of the anterior engaging segment and an apex portion posterior to the anterior dentition of the mandibular arch,
   said pyramidal segment extending at said predetermined angle for a length sufficient to maintain the downwardly extending segment posterior to the anterior teeth of the manibular arch.

3. An appliance for correcting oral malocclusions according to claim 2 wherein said pyramidal segment is shaped to avoid contact with soft tissue in the mandibular arch.

4. An appliance for correcting oral malocclusions according to claim 3 wherein the labial facing surface of each pyramidal segment includes a beveled lateral inferior portion for avoiding contact of the pyramidal segment with the soft tissue of the mandibular arch while the angle of the inclined plane is maintained.

5. An appliance for correcting oral malocclusions according to claim 1 further comprising at least one segment extending posteriorly from said the maxillary arch anterior dentition engaging segment running substantially parallel to the palatal arch but spaced therefrom to avoid contact with soft tissue in the maxillary arch.

6. An appliance for correcting oral malocclusions according to claim 1 wherein each downwardly extending segment includes a plurality of longitudinal ridges running across the labial facing surface at a point along the labial facing surface to correct a prescribed type of malocclusion.

7. An appliance for correcting oral malocclusions according to claim 6 wherein each downwardly extending segment includes first, second and third longitudinal ridges, said first longitudinal ridge being located above said second and third longitudinal ridges for treatment of Class II Division 1 malocclusions, said third longitudinal ridge being located below said first and second longitudinal ridges for treatment of Class II Division 2 malocclusions, and said second longitudinal ridge being located intermediate said first and second longitudinal ridges for treatment of Class I malocclusions.

8. An appliance for correcting oral malocclusions according to claim 1 wherein the labial facing surface of each descending segment contacts the lingual aspect of an incisal edge of a selected tooth in the mandibular arch having a positional irregularity at a prescribed angle with respect to the tooth to urge said tooth into correct positional alignment.

9. An appliance for correcting oral malocclusions according to claim 1 further comprising at least one wedge shaped segment adapted to be joined to and cover the labial facing surface of one of said downwardly extending segments to form an inclined plane forward of the labial facing surface of the downwardly extending segment for contacting the lingual aspect of an incisor or cuspid on the mandibular arch.

10. An appliance for correcting oral abnormalities comprising:

a first segment for engaging anterior dentition of the maxillary arch;

a pair of spaced substantially parallel second segments extending downwardly and posteriorly from the anterior dentition engaging segment at a predetermined angle with respect to the anterior dentition engaging segment;

each second segment including a substantially flat labial facing surface forming a ramp at said predetermined angle with said anterior dentition engaging segment for contacting the lingual aspect of an incisor or cuspid on the mandibular arch to urge the mandible forward and upward;

at least one ridge extending across each second segment labial facing surface substantially parallel with said first segment at a prescribed location along said labial facing surface to restrict the forward and upward movement of the mandible when said mandibular lateral incisor or cuspid is in contact with the labial facing surface; and a pair of spaced substantially parallel third segments extending posteriorly from said anterior dentition engaging segment spaced from and running along the palatal arch to prevent swallowing of the appliance.

11. An appliance for correcting oral abnormalities according to claim 10 wherein each second segment comprises a generally pyramidal shaped segment having a base portion joined to the lower end of the first anterior dentition engaging segment and an apex portion posterior to the anterior dentition of the mandibular arch, each pyramidal segment being of a length sufficient to maintain a position posterior to the anterior teeth of the mandibular arch.

12. An appliance for correcting oral abnormalities according to claim 11 wherein each pyramidal segment has a triangular cross-section shaped to be spaced from the soft tissue in the mandibular arch.

13. An appliance for correcting oral abnormalities according to claim 10 wherein each second segment includes a plurality of ridges running across the labial facing surface substantially parallel to said first anterior dentition engaging segment each being at a position along the labial facing surface for limiting the travel of the lower jaw to correct a prescribed type of malocclusion.

14. An appliance for correcting oral abnormalities according to claim 13 wherein each second segment includes first, second and third longitudinal ridges, said first longitudinal ridge being positioned above said second and third longitudinal ridges for treatment of Class II Division 1 malocclusions, said third longitudinal ridge being positioned below said first and second longitudinal ridges for treatment of Class II Division 2 malocclusions, and said second longitudinal ridge being positioned intermediate said first and third longitudinal ridges for treatment of Class I malocclusions.

15. An appliance for correcting oral abnormalities according to claim 10 wherein the labial facing surface of each second segment is angled with respect to the lingual aspect of an incisal edge of a selected tooth in the mandibular arch having a positional irregularity to urge said tooth into correct positional alignment.

16. An appliance for correcting oral abnormalities according to claim 15 wherein the selected tooth is a mandibular lateral incisor or a cuspid.

17. An appliance for correcting oral abnormalities according to claim 10 wherein the first segment comprises a surface in contact with the labial facing surfaces of the anterior dentition of the maxillary arch and a surface in contact with the lingual facing surfaces of the anterior dentition of the maxillary arch.

18. An appliance for correcting oral abnormalities according to claim 17 wherein the first segment surface is contact with a portion of the lingual surfaces of the anterior dentition of the maxillary arch and the first segment surface in contact with the labial facing surfaces of the anterior dentition of the maxillary arch are formed by placing uncured acrylic between posterior extending portion of the first segment and the labial facing portion of the first segment, forcing the uncured acrylic in the first segment into contact with the anterior dentition of the maxillary arch, removing said first segment from the anterior dentition of the maxillary arch and bench curing the uncured acrylic.

19. An appliance for correcting oral abnormalities according to claim 10 further comprising a pair of plates each for being joined to the labial surface of a second segment to form a ramp at a prescribed distance forward of the labial surface of said second segment for contacting the lingual aspect of an incisor or cuspid on the mandibular arch.

* * * * *